(12) United States Patent
Shamloo (10) Patent No.: US 10,314,669 B1
(45) Date of Patent: Jun. 11, 2019

(54) RETRACTABLE PROTECTIVE COVERING ASSEMBLY FOR SELECTIVELY EXPOSING A WORKING END OF A DENTAL INSTRUMENT

(71) Applicant: Shahram Shamloo, East Norriton, PA (US)

(72) Inventor: Shahram Shamloo, East Norriton, PA (US)

( * ) Notice: Subject to any disclaimer, the term of this patent is extended or adjusted under 35 U.S.C. 154(b) by 0 days.

(21) Appl. No.: 15/850,424

(22) Filed: Dec. 21, 2017

(51) Int. Cl.
  *A61C 1/16* (2006.01)
  *A61C 19/04* (2006.01)

(52) U.S. Cl.
  CPC .............. *A61C 1/16* (2013.01); *A61C 19/04* (2013.01)

(58) Field of Classification Search
  CPC .......... A61B 17/3496; A61B 5/150633; A61B 5/150664; A61B 5/150656; A61B 5/150534; A61B 2017/00336; A61C 7/02; A61C 3/12; A61C 3/10; A61C 3/08; A61C 3/00; A61C 19/043; A61C 19/04; A61C 19/02; A61C 5/40; A61C 5/50; A61C 1/16; A61C 2202/00; A61C 2204/00; A61C 15/02; A61M 5/3216
  USPC ................................................. 433/116, 141
  See application file for complete search history.

(56) References Cited

U.S. PATENT DOCUMENTS

| | | | | |
|---|---|---|---|---|
| 383,367 A * | 5/1888 | Patrick | ..................... | A61C 1/16 433/116 |
| 525,278 A * | 8/1894 | Peck | ........................ | A61C 1/16 433/116 |
| 2,187,442 A * | 1/1940 | Beach | ................... | A61C 15/046 132/326 |
| 5,029,358 A * | 7/1991 | Zimmerman | ............ | A46B 7/04 15/106 |
| 5,283,924 A * | 2/1994 | Kaminski | ............... | A46B 9/005 15/167.1 |
| 5,603,699 A * | 2/1997 | Shine | ................... | A61M 5/3216 604/110 |
| 6,120,482 A * | 9/2000 | Szabo | ................. | A61M 5/3216 128/919 |
| 2003/0181861 A1* | 9/2003 | Wilkinson | .......... | A61M 5/3216 604/192 |
| 2003/0181868 A1* | 9/2003 | Swenson | ............. | A61M 5/3216 604/263 |

(Continued)

*Primary Examiner* — Wade Miles
*Assistant Examiner* — Shannel N Wright
(74) *Attorney, Agent, or Firm* — Glenn E. Gold, P.A.; Glenn E. Gold (57) ABSTRACT

A retractable protective covering assembly enabling a dental operator to selectively expose and cover a distal portion of a working end of a dental instrument during an intraoral examination of a dental patient, including a base component releasably attachable about the exterior of a length of a rigid linear shaft of the dental instrument, a cover component coupled to the base component, a coupling mechanism coupling the cover component to the base component, and a biasing element interposed between a proximal end of the cover component and an exterior surface the dental instrument rigid linear shaft, wherein the biasing element exerts a generally upward force against the proximal end portion of the cover component and urges a dental working end cover portion downwardly such that a distal end portion of the dental working end cover portion extends below the working end distal portion of the dental instrument.

18 Claims, 5 Drawing Sheets

(56) References Cited

U.S. PATENT DOCUMENTS

2013/0020218 A1\* 1/2013 Brilliant ................ A61C 15/02
206/380

\* cited by examiner

RETRACTABLE PROTECTIVE COVERING ASSEMBLY FOR SELECTIVELY EXPOSING A WORKING END OF A DENTAL INSTRUMENT

FIELD OF THE INVENTION

The present invention pertains to dental instruments, such as dental explorers, used by dental operators to conduct intraoral patient examinations. More particularly, the invention relates to minimizing injury to intraoral tissue (and related) damage resulting from accidental, or other inadvertent, contact between a sharp working end of such a dental instrument with intraoral (and related) tissue of a patient during a dental examination.

BACKGROUND OF THE INVENTION

A dental explorer (alternatively referred to herein as an "explorer") is a sharp, pointed metallic instruments so designed that various surfaces of the teeth may be conveniently reached with the explorer point. The explorer provides the tactile information to the clinician's fingers and is used to locate calculus deposits, tooth surface irregularities, defective margins on restorations, decalcified areas, and carious lesions.

Dental explorers are generally composed of a handle (or shaft), a shank and a calibrated working end. The handle (alternately referred to as the "shaft") is the part grasped in the operator's hand, usually straight and without variation in size, smooth knurled and/or serrated to allow for better instrument control. The shank begins with the first twisted portion of the shaft and ends where the nib or blade begins. Typically, it may be straight, single, double or triple angled. It tapers smoothly from the shaft to the nib/blade. The nib or blade is the working part of the instrument and begins at the last angle, which terminates the shank.

Three different explorers are commonly used in dentistry. One, commonly referred to as the "number 23" explorer, ends in a semicircle tapering to a point at its distal end. The working end of the other two general types of dental explorers commonly referred to as the "number 6" and "number 17" explorers, are shorter, straight, and extend at an angle to the handle. Different types of explorers are differentiated from one another by the design of the working end. Some examples include, but are not limited to, straight explorers, interproximal probes, cow horn (or arch) explorers, back action explorers, shepherds hook explorers and orban-type explorers.

The working ends of such dental instruments are very sharp and, accordingly, can very easily cause injury to the gums, tongue, and other sensitive tissues within a patient's mouth. While this has not been considered a major concern, since most patients are able to maintain their head in a fixed position during such an examination, it is well known amongst dental professionals that some patients are prone to jerking, or otherwise moving, their head during such an examination. For instance, when using this instrument on children or mentally challenged individuals, there is a higher risk of accidental injury to soft tissue in the mouth than there is while examining a mature or so-called normal patient. Children and disabled individuals have a tendency to move their heads more often and without notice, especially when they are nervous, upset or crying. If the dental explorer is in the mouth during an examination by an operator (e.g. a dentist or dental hygienist) and the patient jerks their head or moves uncontrollably, the dental explorer can prick or cause injury to the soft tissue of the oral cavity. Presently, the operator is relegated to trying to quickly and carefully remove the working end of the dental explorer from the oral cavity while attempting to avoid soft tissue damage. Obviously, this is simply impossible in most cases since the sharp working end of the instrument is directly exposed to the patient's oral cavity until it has been removed. Furthermore, even in instances where the operator has the reflexes, dexterity and sheer luck, to move the working end of the instrument from intraoral cavity without scraping against any intraoral tissue, there remains a high likelihood of damage to the patient's lips during extraction from the mouth.

Accordingly, there is a need in the dental industry for a solution to this common problem. Accordingly, it would be highly desirable to provide a means for enabling operators of dental explorers to efficiently and effectively create a protective barrier between a sharp working end of such a dental instrument and intraoral tissues within a patient's mouth such that the likelihood of intraoral tissue damage is greatly reduced—and preferably virtually eliminated. It would be further desirable to provide such a solution that does not have a limitation of negatively impacting the operator's ability to conduct the examination. Still further, it would be highly beneficial to provide such a solution having a design amenable to being easily retrofitted, or selectively attached, to existing conventional dental explorer instruments.

SUMMARY OF THE INVENTION

The present invention provides a retractable protective covering assembly for enabling a dental operator to selectively expose and cover a distal portion of a working end of a dental instrument during an intraoral examination of a dental patient. Generally, the dental instrument includes a rigid linear shaft having an exterior surface, opposite shaft ends, a shank portion extending from at least one of the opposite ends, and a working end extending from the shank portion and terminating at a working end distal portion.

The retractable protective covering assembly may comprise:

(a) at least one base component releasably attachable about a length of the dental instrument rigid linear shaft;

(b) a cover component coupled to the base component, the cover component extending parallel to a central longitudinal axis of the dental instrument rigid linear shaft and in a direction from a proximal end portion of the cover component toward the shank portion and working end of the dental instrument, the cover component having a dental working end cover portion at a distal end thereof;

(c) a coupling mechanism coupling the cover component to the base component in a manner enabling pivotal rotation of the cover component vis-à-vis said base component; and (d) a biasing element interposed between the cover component proximal end portion and the exterior surface of the dental instrument rigid linear shaft, wherein the biasing element exerts a generally upward force against the proximal end portion of the cover component adequate to cause a gap between the proximal end portion of the cover component and the dental instrument rigid linear shaft, wherein the upward force exerted by the biasing element against the proximal end portion of the cover component correspondingly urges the dental working end cover portion downwardly such that a distal end portion of the dental working end cover portion extends below the working end distal portion of the dental instrument.

In an aspect, the at least one base component may further comprise a pair of base components.

In another aspect, each one of the pair of base components may further comprise a curved unitary structure having a forward end, a rear end, an upper end, an upper edge, a lower edge, an exterior surface and an interior surface, the interior surface being contoured to conform with a corresponding contour of the exterior surface of the rigid linear shaft of the dental instrument.

In another aspect, the pair of base components may be positioned against the exterior surface along lateral portions of the rigid linear shaft of the dental instrument, the cover component may be positioned against the exterior surface along an upper portion of the rigid linear shaft of the dental instrument and interposed between said pair of base components, and the coupling mechanism may be sized, shaped and otherwise configured to couple the cover component to the pair of base components in a manner enabling rotation of the cover component about the coupling mechanism.

In another aspect, the coupling element may comprise a linear rigid pin.

In another aspect, the biasing element may further comprise at least one of a compression spring and a resilient body.

In another aspect, the cover component may further comprise a unitary cover component defined by an angled proximal first length transitioning into a second straight intermediate length transitioning into said dental working end cover portion.

In a further implementation, a dental instrument assembly may be provided for enabling a dental operator to selectively expose and cover a distal portion of a working end of the dental instrument during an intraoral examination of a dental patient, the dental instrument assembly comprising:

(a) a dental instrument having a rigid linear shaft having an exterior surface, opposite shaft ends, a shank portion extending from at least one of the opposite ends, and a working end extending from the shank portion and terminating at a working end distal portion; and (b) a retractable protective covering subassembly, including:

at least one base component releasably attachable about a length of the dental instrument rigid linear shaft;

a cover component coupled to the base component, the cover component extending parallel to a central longitudinal axis of the dental instrument rigid linear shaft and in a direction from a proximal end portion of the cover component toward the shank portion and working end of the dental instrument, the cover component having a dental working end cover portion at a distal end thereof;

a coupling mechanism coupling the cover component to the base component in a manner enabling pivotal rotation of the cover component vis-à-vis the base component; and a biasing element interposed between the cover component proximal end portion and the exterior surface of the dental instrument rigid linear shaft, wherein the biasing element exerts a generally upward force against the proximal end portion of the cover component adequate to cause a gap between the proximal end portion of the cover component and the dental instrument rigid linear shaft, the upward force exerted by the biasing element against the proximal end portion of the cover component correspondingly urging the dental working end cover portion downwardly such that a distal end portion of the dental working end cover portion extends below the working end distal portion of the dental instrument.

In another aspect, the retractable protective covering may be incorporated as a separate assembly for selective attachment to an existing dental explorer or as an assembly integrated as part of the dental explorer.

In another aspect, the retractable protective covering may be provided in the form of a children's character or the like, for example, for use in a pediatric dental setting.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF EXEMPLARY IMPLEMENTATIONS

Figure 1:
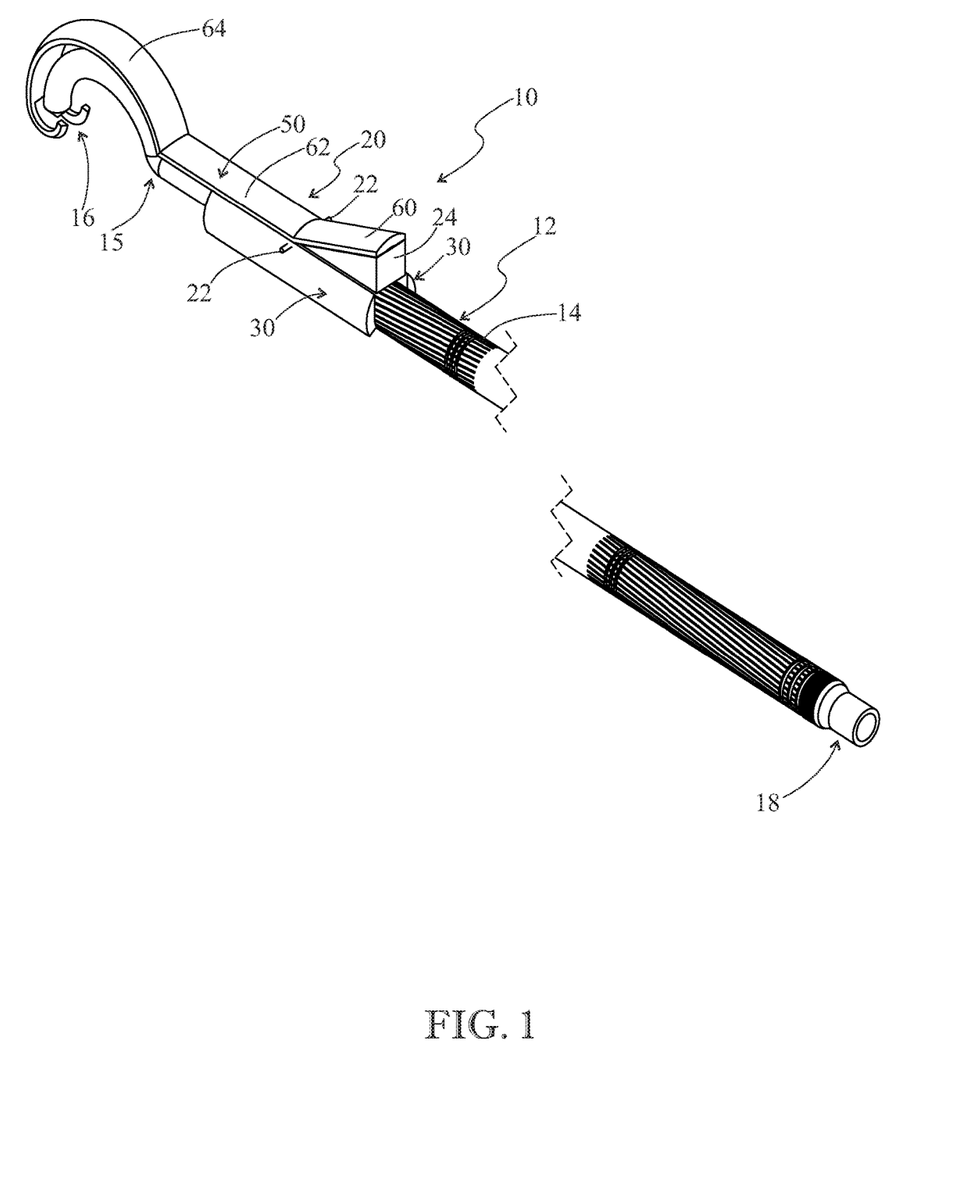
FIG. 1 is a top rear perspective view of a dental explorer having a retractable protective covering assembly in accordance with a first exemplary implementation.
Figure 2:
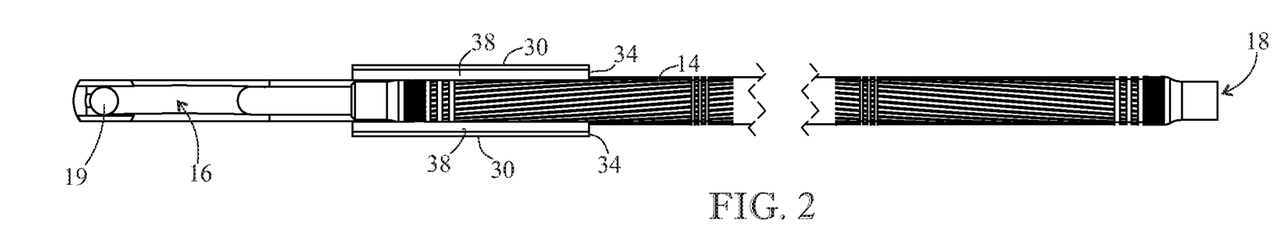
FIG. 2 is a left side elevation view of the dental explorer and retractable protective covering assembly initially introduced in FIG. 1.
Figures 3, 4:
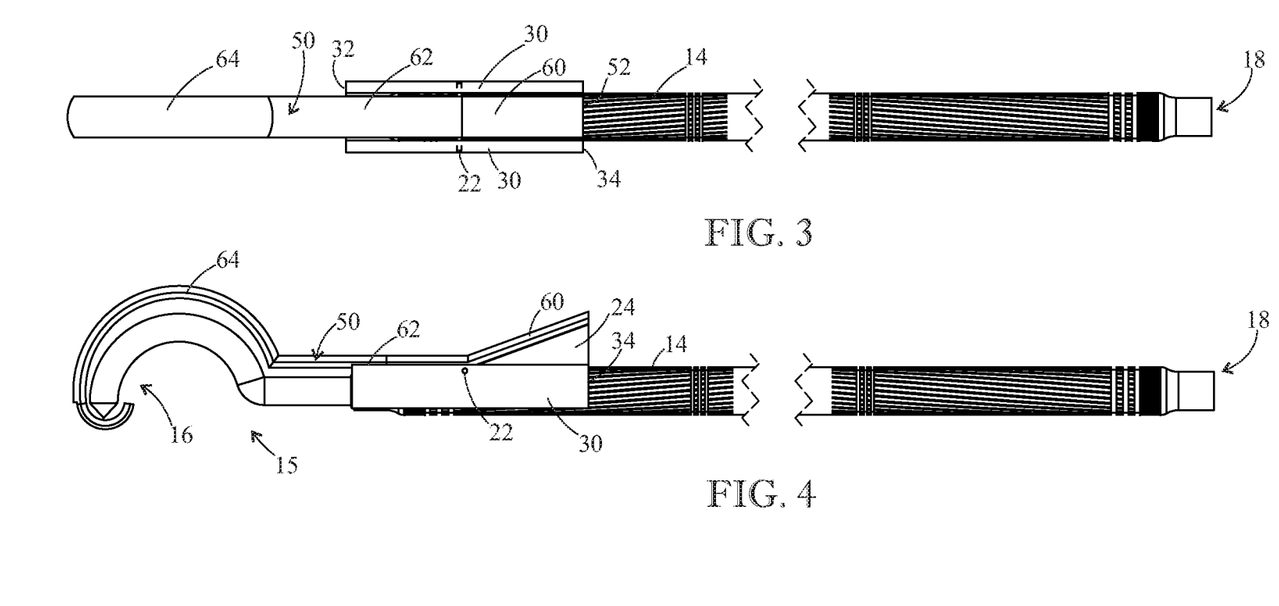
FIG. 3 is a top plan view thereof.
FIG. 4 is a bottom plan view thereof.
Figure 5:
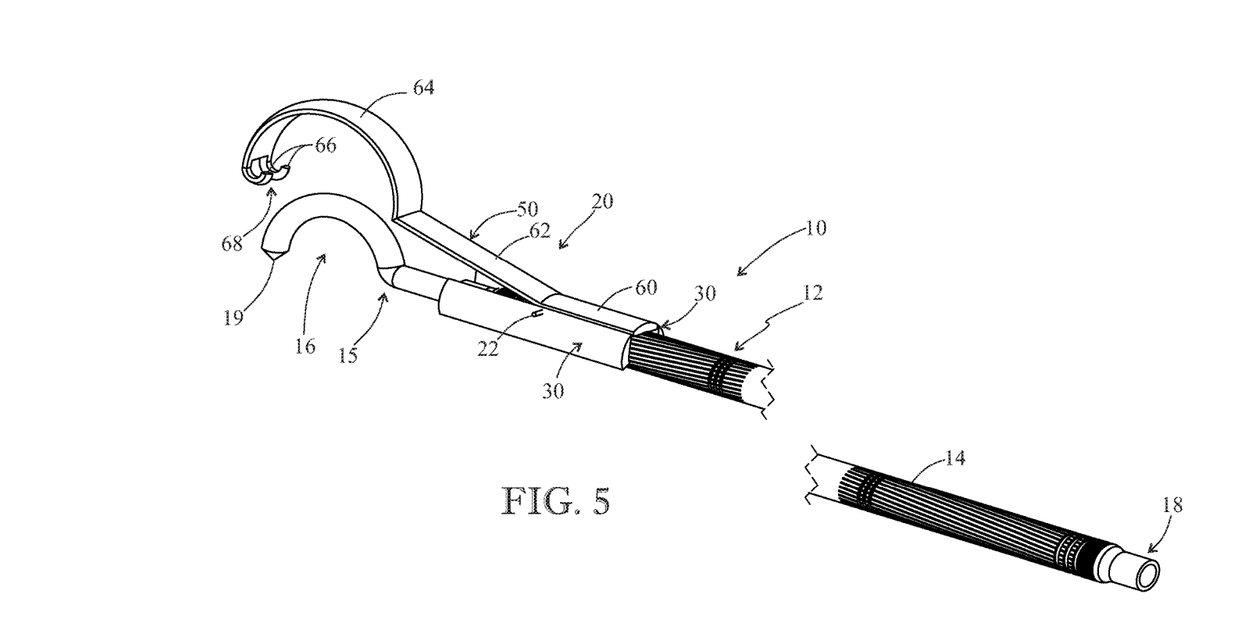
FIG. 5 is a top rear perspective view of the dental explorer and retractable protective covering assembly initially introduced in FIG. 1, showing the retractable protective covering assembly in a retracted position to expose a distal portion of the working end of the dental explorer.
Figure 6:
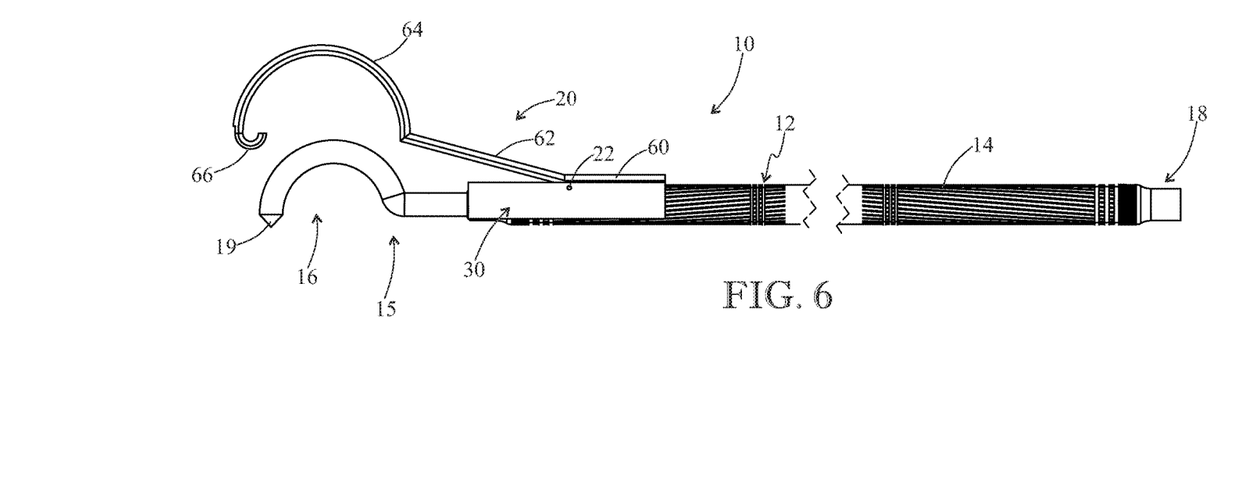
FIG. 6 is a left side elevation view of the dental explorer and retractable protective covering assembly shown in FIG. 5.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring to FIGS. 1-9 and, initially, particularly to FIGS. 1-4, the present invention provides a retractable protective covering and dental explorer assembly, shown generally as reference number 10, which includes a retractable protective cover assembly 20 coupled to a dental explorer 12. The dental explorer 12, a dental instrument that is well known in the dental arts, may include a handle 14 (alternatively referred to as a "shaft"), a shank portion 15, and a working end 16 (shown here in the form of a nib). As used herein, the term "nib" refers to the curved length extending from shank 15 and terminating at distal tip (or point) 19. Although the exemplary implementation is shown depicting a working end 16 in the form of a nib, it will be appreciated by those skilled in the dental arts that the retractable protective cover assembly of the present invention could be employed for use with a variety of types of dental explorers incorporating a variety of working end structures (such as, for example, those described hereinabove in the Background of the Invention section), without departing from the intended scope of the invention. For that matter, the retractable protective cover assembly of the present invention could be adapted for use with a host of dental instruments beyond dental explorers. The drawing figures depict a working end 16 at only one end of the dental explorer 12 for the sake of convenience. However, a shank and nib structure, or other working end structure, could likewise be provided extending from the opposite end 18 of the dental explorer 12.

Figure 7:
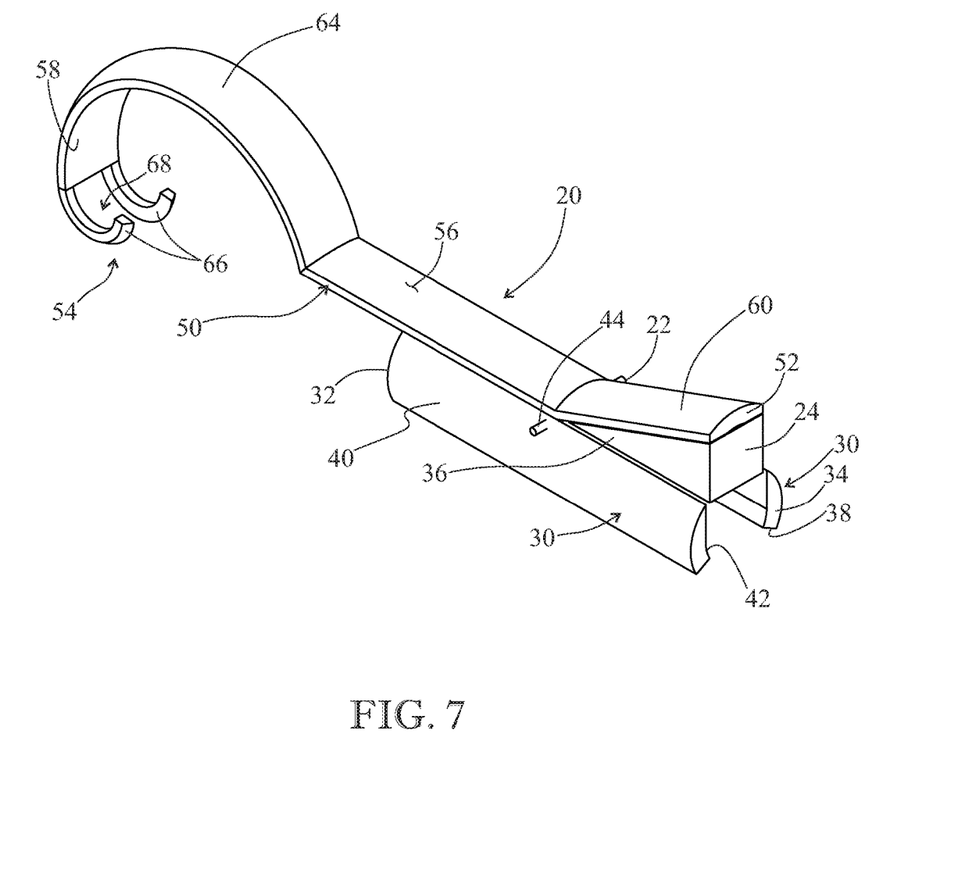
FIG. 7 is a top rear perspective view of a retractable protective covering assembly in accordance with an exemplary implementation, shown fully assembled but removed from a dental explorer.
Figure 8:
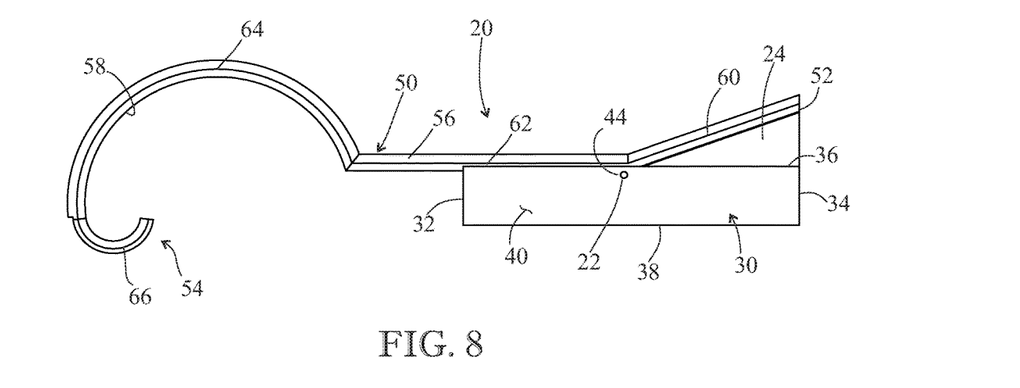
FIG. 8 is a left side elevation view of the retractable protective covering assembly shown in FIG. 7.
Figure 9:
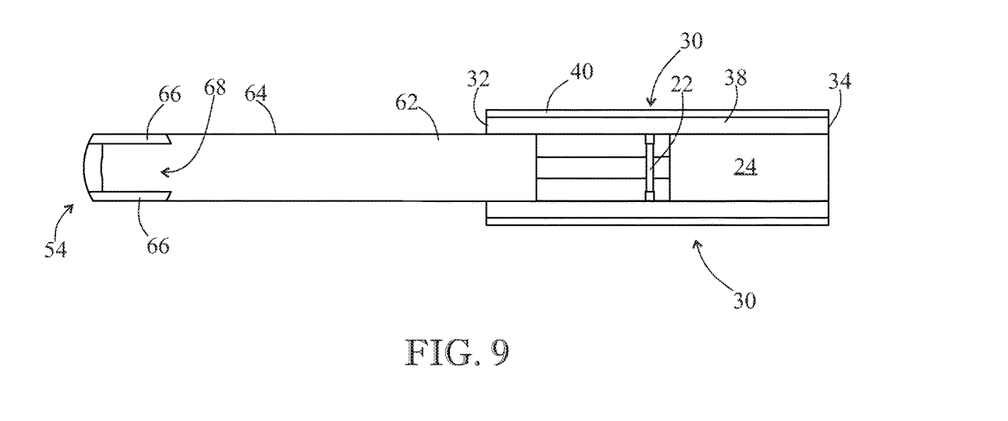
FIG. 9 is a bottom plan view thereof.

Referring now to FIGS. 1-9, and as best shown in FIGS. 7-9, the exemplary retractable cover assembly 20 may include base components 30 (alternately referred to herein as "attachment components"), unitary retractable cover 50, coupling pin 22 and biasing component 24. In the exemplary implementation, and as described in more detail hereinbelow, pin 22 is used to couple base/attachment components 30 to unitary retractable cover 50. Each attachment base component 30 may have a geometry at least partially defined by forward end 32, rear end 34, upper edge 36, lower edge 38, exterior surface 40, and interior surface 42. Preferably, interior surface 42 is provided having a curvature conforming to curved exterior surface 40 of dental explorer handle/shaft 14. Although exterior surface 40 of base/attachment components 30 is shown having a smoothly curved shape, the exterior surface could be provided having any surface geometry that does not impede the intended functionality of the retractable cover assembly 20.

As called out in FIGS. 7 and 8, each base/attachment component 30 is provided having an aperture 44 extending therethrough, and in linear alignment with corresponding apertures (not shown) extending through unitary retractable cover 50, such that pin 22 extends completely through apertures 44 and the linearly-aligned apertures (not shown) extending through unitary retractable cover 50 to effectively couple the base components 30 with the unitary retractable cover as well as to facilitate the attachment of the unitary retractable cover about the exterior surface of the handle 14 of the dental explorer 12. As shown in the exemplary implementation, each aperture 44 may be located proximate upper edge 36 of base/attachment component 30. The opposite ends of pin 22 may be bent, crimped or otherwise manipulated to prevent pin 22 from being inadvertently slidably removed. Likewise, an endcap (not shown) or similar element may be provided at each of the opposite ends of pin 22 to provide the same function.

Referring now to FIGS. 1-9, and as best shown in FIGS. 7-9, unitary retractable cover 50 is generally defined by a proximal end 52, a distal end 54, an exterior surface 56 and an interior surface 58. Furthermore, along its length unitary retractable cover may be further defined by an angled, or tapered, first length 60 transitioning into straight second length 62, which then transitions into working end cover portion 64. At its distal end 54 the working end cover portion 64 of unitary retractable cover 50 terminates at a pair of spaced-apart curved prongs 66 defining a gap 68 therebetween. As is further described hereinbelow, the gap 68 has a gap length slightly greater than the diameter of working end, or nib 16, of the dental explorer 12 to enable the working end cover portion 64 to be retracted to expose tip 19 and a distal portion of nib 16 without being impeded by the working end cover portion.

As shown in FIGS. 1-9, a biasing element 24 is provided interposed between the interior surface 58 of angled/tapered first length 60 of unitary retractable cover 50 and the exterior surface of handle 14. The biasing element 24 may be provided in the form of a resilient wedge as shown in accordance with the exemplary implementation. However, alternate biasing element forms are contemplated. For example, in lieu of a resilient wedge, biasing component 24 may be provided in the form of a compression spring. What is most important is that the biasing component 24 exerts a generally upward force against the proximal end portion 60 of the unitary retractable cover 50 adequate to create a gap between the interior surface 58 of the angled/tapered length 60 of the unitary retractable cover 50 and the exterior surface of the dental instrument rigid linear shaft 14, whereby the upward force exerted by the biasing element 24 against the interior surface of the angled/tapered length 60 of the unitary retractable cover 50 correspondingly urges the dental working end cover portion 64 downwardly such that the working end cover portion 64 extends below the corresponding working end 16 of dental explorer 12 to effectively cover point/tip 19 of nib 16 and thereby provide protective covering. In other words, absent the application of a downward (e.g. pressing) force upon angled/tapered length 60 of unitary retractable cover 50, biasing component 24 creates a counter-clockwise (using the orientation shown in FIGS. 1-6) rotational force against cover 50 about a central axis of pin 22.

Likewise, in order to selectively expose tip 19 and corresponding nib 16, a dental operator merely has to apply a generally downward (pressing) force against the exterior surface 56 of angled/tapered length 60 of unitary retractable cover 50. The downward force exerted by the dental operator against the exterior surface of the angled/tapered length 60 of the unitary retractable cover 50 correspondingly urges the dental working end cover portion 64 upwardly such that the working end cover portion 64 is retracted to a position above the corresponding working end 16 of dental explorer 12 to effectively expose point/tip 19 of nib 16 and thereby enable the dental operator to utilize the dental explorer to conduct an intraoral examination of a patient's mouth. In other words, with the application of a downward (e.g. pressing) force upon angled/tapered length 60 of unitary retractable cover 50, biasing component 24 is compressed to enable a clockwise (using the orientation shown in FIGS. 1-6) rotational force against cover 50 about a central axis of pin 22.

Although the present invention has been shown and described in accordance with an exemplary implementation, the invention is not intended to be so limiting. For instance, applicant contemplates use of a retractable dental instrument (e.g. dental explorer) cover in the form of a compression spring encapsulated within a resilient sleeve, wherein the sleeve-encapsulated spring is disposed about the working end and at least a portion of the dental instrument and is in communication with a biasing element enabling a dental operator to selectively retract an opening at a distal end of the sleeve encapsulated spring to expose the dental explorer tip.

Furthermore, although the invention has been shown and described in accordance with an exemplary implementation wherein the protective covering assembly is a separate assembly particularly configured to be selectively attached to an existing dental explorer, the invention is not intended to be so limiting. In that regard, it will be apparent to those skilled in the dental arts that the protective covering assembly may be provided directly integrated with a dental explorer.

Since many modifications, variations, and changes in detail can be made to describe preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A retractable protective covering assembly for enabling a dental operator to selectively expose and cover a distal portion of a working end of a dental instrument during an intraoral examination of a dental patient, the dental instrument including a rigid linear shaft having an exterior surface, opposite shaft ends, a shank portion extending from at least one of the opposite ends, and a working end extending from the shank portion and terminating at a working end distal portion, the retractable protective covering assembly comprising:
    at least one base component releasably attachable about a length of said dental instrument rigid linear shaft;
    a cover component coupled to said base component, said cover component extending parallel to a central longitudinal axis of said dental instrument rigid linear shaft and in a direction from a proximal end portion of said cover component toward said shank portion and working end of said dental instrument, said cover component having a dental working end cover portion at a distal end thereof;
    a coupling mechanism coupling said cover component to said base component in a manner enabling pivotal rotation of said cover component vis-à-vis said base component; and
    a biasing element interposed between said cover component proximal end portion and the exterior surface of said dental instrument rigid linear shaft, wherein said biasing element exerts a generally upward force against said proximal end portion of said cover component adequate to cause a gap between said proximal end portion of said cover component and said dental instrument rigid linear shaft, said upward force exerted by said biasing element against the proximal end portion of said cover component correspondingly urging said dental working end cover portion downwardly such that a distal end portion of said dental working end cover portion extends below the working end distal portion of said dental instrument.

2. A retractable protective covering assembly as recited in claim 1, wherein said at least one base component further comprises a pair of base components.

3. A retractable protective covering assembly as recited in claim 2, wherein each one of said pair of base components further comprises a curved unitary structure having a forward end, a rear end, an upper end, an upper edge, a lower edge, an exterior surface and an interior surface, said interior surface contoured to conform with a corresponding contour of the exterior surface of the rigid linear shaft of the dental instrument.

4. A retractable protective covering assembly as recited in claim 2, wherein said pair of base components are positioned against the exterior surface along lateral portions of the rigid linear shaft of the dental instrument, the cover component is positioned against the exterior surface along an upper portion of the rigid linear shaft of the dental instrument and interposed between said pair of base components, and said coupling mechanism is sized, shaped and otherwise configured to couple said cover component to said pair of base components in a manner enabling rotation of said cover component about said coupling mechanism.

5. A retractable protective covering assembly as recited in claim 3, wherein said pair of base components are positioned against the exterior surface along lateral portions of the rigid linear shaft of the dental instrument, said cover component is positioned against the exterior surface along an upper portion of the rigid linear shaft of the dental instrument and is interposed between said pair of base components, and said coupling mechanism is sized, shaped and otherwise configured to couple said cover component to said pair of base components.

6. A retractable protective covering assembly as recited in claim 4, wherein said coupling element further comprises a linear rigid pin.

7. A retractable protective covering assembly as recited in claim 5, wherein said coupling element further comprises a linear rigid pin.

8. A retractable protective covering assembly as recited in claim 1, wherein said biasing element further comprises at least one of a compression spring and a resilient body.

9. A retractable protective covering assembly as recited in claim 8, wherein said cover component further comprises a unitary cover component defined by an angled proximal first length transitioning into a second straight intermediate length transitioning into said dental working end cover portion.

10. A dental instrument assembly for enabling a dental operator to selectively expose and cover a distal portion of a working end of the dental instrument during an intraoral examination of a dental patient, the dental instrument assembly comprising:
    a dental instrument including a rigid linear shaft having an exterior surface, opposite shaft ends, a shank portion extending from at least one of the opposite ends, and a working end extending from the shank portion and terminating at a working end distal portion; and
    a retractable protective covering subassembly, including:
        at least one base component releasably attachable about a length of said dental instrument rigid linear shaft;
        a cover component coupled to said base component, said cover component extending parallel to a central longitudinal axis of said dental instrument rigid linear shaft and in a direction from a proximal end portion of said cover component toward said shank portion and working end of said dental instrument, said cover component having a dental working end cover portion at a distal end thereof;

a coupling mechanism coupling said cover component to said base component in a manner enabling pivotal rotation of said cover component vis-à-vis said base component; and a biasing element interposed between said cover component proximal end portion and the exterior surface of said dental instrument rigid linear shaft, wherein said biasing element exerts a generally upward force against said proximal end portion of said cover component adequate to cause a gap between said proximal end portion of said cover component and said dental instrument rigid linear shaft, said upward force exerted by said biasing element against the proximal end portion of said cover component correspondingly urging said dental working end cover portion downwardly such that a distal end portion of said dental working end cover portion extends below the working end distal portion of said dental instrument.

11. A dental instrument assembly as recited in claim 10, wherein said at least one base component further comprises a pair of base components.

12. A dental instrument assembly as recited in claim 11, wherein each one of said pair of base components further comprises a curved unitary structure having a forward end, a rear end, an upper end, an upper edge, a lower edge, an exterior surface and an interior surface, said interior surface contoured to conform with a corresponding contour of the exterior surface of the rigid linear shaft of the dental instrument.

13. A dental instrument assembly as recited in claim 11, wherein said pair of base components are positioned against the exterior surface along lateral portions of the rigid linear shaft of the dental instrument, the cover component is positioned against the exterior surface along an upper portion of the rigid linear shaft of the dental instrument and interposed between said pair of base components, and said coupling mechanism is sized, shaped and otherwise configured to couple said cover component to said pair of base components in a manner enabling rotation of said cover component about said coupling mechanism.

14. A dental instrument assembly as recited in claim 12, wherein said pair of base components are positioned against the exterior surface along lateral portions of the rigid linear shaft of the dental instrument, said cover component is positioned against the exterior surface along an upper portion of the rigid linear shaft of the dental instrument and is interposed between said pair of base components, and said coupling mechanism is sized, shaped and otherwise configured to couple said cover component to said pair of base components.

15. A dental instrument assembly as recited in claim 13, wherein said coupling element further comprises a linear rigid pin.

16. A dental instrument assembly as recited in claim 14, wherein said coupling element further comprises a linear rigid pin.

17. A dental instrument assembly as recited in claim 10, wherein said biasing element further comprises at least one of a compression spring and a resilient body.

18. A dental instrument assembly as recited in claim 17, wherein said cover component further comprises a unitary cover component defined by an angled proximal first length transitioning into a second straight intermediate length transitioning into said dental working end cover portion.

* * * * *